United States Patent [19]

Komor et al.

[11] Patent Number: 4,767,741

[45] Date of Patent: Aug. 30, 1988

[54] TWO-PHASE LIQUID COSMETIC AND METHOD OF PREPARING SAME

[75] Inventors: Joseph A. Komor, Ramsey; Philip Franco, Paramus; Lorraine P. Nangle, Clifton; William H. Koelle, Morris Plains, all of N.J.

[73] Assignee: Avon Products, Inc., New York, N.Y.

[21] Appl. No.: 896,708

[22] Filed: Aug. 15, 1986

[51] Int. Cl.$^4$ ............................ A61K 7/46; A61K 7/00
[52] U.S. Cl. ........................................ 512/3; 252/308;
  252/315.1; 252/315.4; 424/59; 424/70; 424/78;
  424/401; 512/1; 514/847; 514/937; 514/939;
  514/942; 514/943
[58] Field of Search ............... 252/522 R, 308, 315.1,
  252/315.4; 424/78, 70, 59; 514/847, 937, 939,
  943, 942

[56] References Cited

U.S. PATENT DOCUMENTS 3,920,883 11/1975 Yamada et al. ................. 424/78
4,563,346 1/1986 Deckner .......................... 252/522 R

*Primary Examiner*—Werren B. Lone
*Assistant Examiner*—Vera C. Clarke
*Attorney, Agent, or Firm*—S. MIchael Bender

[57] ABSTRACT

A two-phase liquid cosmetic composition is provided comprising an oil phase, an organic liquid/water phase, and insoluble solid particles absorbed on the interface between the two phases wherein the solid particles comprise the in situ precipitation product of at least first and second salt solutions added to the oil phase and organic liquid/water phase during blending thereof. The insoluble salt precipitates facilitate dispersion of the oil phase in the form of "spheres" or "droplets" within the organic liquid/water phase thereby producing a liquid cosmetic having an aesthetically desirable appearance.

9 Claims, No Drawings

TWO-PHASE LIQUID COSMETIC AND METHOD OF PREPARING SAME

TECHNICAL FIELD

The present invention relates generally to cosmetic preparations, and more particularly, to a novel liquid, two-phase composition wherein one phase comprises oil, the other phase comprises an organic liquid (e.g., alcohol, water and fragrance), and wherein insoluble solid particles are disposed at the interface between the two phases thereby stabilizing the oil in the form of small droplets or spheres disposed within the organic liquid phase.

BACKGROUND ART

U.S. Pat. No. 3,920,883 describes an "attractive" liquid cosmetic composition comprising an oil phase, an organic liquid/water phase, and finely divided solid particles insoluble in either the oil or organic liquid phases. According to the patent, the oil will form small "spheres" or "droplets" dispersed throughout the organic aqueous phase which will remain stable if the insoluble solid particles, said to be adsorbed on the interface between the oil phase and the organic liquid phase are selected from a class of certain substances. To make the foregoing composition, the '883 patent recommends that four ingredients, i.e., oil, water, the organic liquid, and the finely divided solid particles be admixed and blended together either sequentially or concurrently using any conventional blending device. However, the preferred method is to mix the water and organic liquid together, followed by addition of the finely divided solid particles. The oil then is added and the entire mixture agitated. Nonetheless, in attempting to follow the teachings of the patent, that is, directly adding the insoluble finely divided particles to the oil-/organic liquid blend, and using particle substances disclosed in the patent, it was found that the oil droplets or "bubbles" formed in the resulting composition were translucent, not transparent; that the "bubbles" had relatively poor stability, i.e., they tended to coalesce; that there was substantial sedimentation of the insoluble solid particles in the final composition product; and that the final composition was far less aesthetically pleasing than desired.

DISCLOSURE OF THE INVENTION

In accordance with the present invention, an improved two-phase liquid cosmetic composition is formed where the insoluble solid particles dispersed at the interface between the oil phase and the organic liquid phase are formed via in situ precipitation during the blending of the two phases. In the preferred method of making the composition of the invention, three different salt solutions, namely, calcium chloride, sodium dodecylbenzenesulfonate, and sodium silicate are added to the oil and organic liquid phases to facilitate in situ precipitation of two insoluble salts, i.e., calcium silicate and calcium dodecylbenzenesulfonate, and one soluble salt, sodium chloride, with the two insoluble salts adhering to the interface between the oil and organic liquid phases, and the soluble salt passing harmlessly into solution. As the insoluble salt particles are precipitated out of solution during blending of the oil, organic liquid, and previously mentioned salt solutions, they become uniformly deposited onto the surface of stable oil spheres contained in the organic liquid phase. Owing to this novel in situ precipitation technique, the "bubbles" or oil droplets formed in the composition of the present invention are extremely clear and transparent to the naked eye, have excellent stability over an extended period of time, and the composition exhibits little or no sedimentation of solid particles. As a result, the formation of stable oil droplets within the organic liquid phase in accordance with the invention yields a cosmetic composition having exceptional aesthetic appeal.

BEST MODE FOR CARRYING OUT THE INVENTION

Prior two-phase compositions useful as cosmetic preparations are fully described in U.S. Pat. No. 3,920,883 the disclosure of which hereby is incorporated herein by this reference. In such prior compositions, an oil phase is dispersed in the form of small droplets or spheres in an organic liquid which may or may not be mixed with water, i.e., the organic liquid is miscible with water whereas the oil is not. In order to give the small spheres a distinctive surface appearance and to maintain their longevity (i.e., stability) in the organic liquid phase, finely divided solid particles are added to the two-phase mixture and are adsorbed onto the interface between the immiscible oil and organic liquid phases.

The essence of the present invention is the discovery that in situ precipitation of certain finely divided insoluble particles disposed at the interface between the oil phase and organic liquid phase produces a dramatically superior two-phase cosmetic composition.

In making the improved composition of the present invention, there is provided as starting materials (i) an oil phase; (ii) an organic liquid phase which includes a cosmetic ingredient such as a fragrance; (iii) a combination of salt solutions which upon reacting with one another produce at least one insoluble salt precipitate adapted to be disposed at the interface of the oil phase and organic liquid phase; and (iv) various other ingredients commonly employed in cosmetic preparations such as U.V. stabilizers and colorants.

The oils used in carrying out the invention may be any of those disclosed in the aforementioned '883 patent, column 3, lines 24–49, or mixtures thereof. Light mineral oil is a high quality emollient, has desirable tactile properties, and offers an attractive appearance when viewed through the transparent walls of a glass container, and therefore, is especially preferred. The amount of light mineral oil used in the composition may be varied to a considerable degree and generally speaking, will depend upon the amount of the organic liquid phase and the desired disposition of the oil spheres dispersed in the latter, i.e., by increasing the amount of oil relative to the amount of organic liquid, the volume of oil spheres dispersed in the organic liquid phase will be increased. In a typical preferred composition useful as a vehicle for a fragrant compound or ingredient, such as a cologne splash, for example, the amount of oil may range as high as about 80% of the composition by weight; however, an amount in the range of about 30% to about 40% by weight will produce an attractive appearance with the oil spheres occupying approximately one-half the apparent volume of the entire liquid composition and is mostly preferred.

Likewise, the organic liquid may comprise any of those identified in the '883 patent, column 4, lines 18–39, or mixtures thereof. Alcohol because it is miscible with both water and most fragrance compounds is especially preferred, with anhydrous ethanol being mostly preferred. Thus, in carrying out the invention, the organic liquid serves not only to contain the dispersed oil spheres, but furthermore, functions as a vehicle or solvent for a cosmetic ingredient such as the aforementioned fragrance compounds. Water may be added to the organic liquid phase to help accommodate certain fragrance or other cosmetic ingredients, and/or to adjust the density (or specific gravity) of the organic liquid phase. At room temperature, the specific gravity of ethanol is about 0.78, the specific gravity of water is 1.0, and the specific gravity of light mineral oil is about 0.83. Preferably water is added to the organic liquid to increase the specific gravity of the organic liquid/aqueous mixture to a level slightly less than that of the oil phase as this will maintain the oil droplets at the bottom or lower one-half of the volume defined by the oil and organic liquid phases. When the oil spheres are so disposed, the resulting composition is quite aesthetically appealing. Thus, in practicing the invention, a sufficient quantity of water may be added to the organic liquid (e.g., ethanol) to maintain the specific gravity of the organic liquid phase less than that of the oil phase (e.g., light mineral oil) by an amount in the range of about 0.005 to 0.015 thereby achieving the preferred dispersion of oil spheres at the bottom or lower half of the organic liquid/water mixture volume. It has been found that the foregoing difference in specific gravity helps to prevent the oil spheres from rising to the top or upper half of the organic liquid/aqueous phase in the presence of decreasing ambient temperatures. It will be appreciated that a sufficient quantity of water should be present in the composition to maintain a density difference in the above range as too great a difference in density between the oil phase and organic liquid/water phase will cause the oil spheres to distort and possibly coalesce. By increasing the ratio of water to ethanol and thereby creating a negative difference between the density of the oil phase vis-a-vis the organic liquid phase, the oil spheres may be made to occupy the upper portion of the organic liquid volume. Similarly, the ethanol/water ratio may be adjusted to create a balance between the density of the oil phase and that of the organic liquid/water phase in which case the oil droplets will appear suspended within the organic liquid phase.

The amount of organic liquid used in the present invention may be as high as about 95% by weight of the composition with an amount in the range of about 40% to about 60% by weight being especially preferred for a cologne spash formulation. In such cases, the amount of fragrance oils added to the organic liquid phase will vary in the range of 4% to about 6% by weight, whereas the amount of water added to the organic liquid will vary in the range of up to about 9% by weight for a condition where the oil spheres occupy the bottom or lower half of the organic liquid/water phase.

In accordance with the present invention and as mentioned above, it has been discovered that stable oil spheres will be formed in the two-phase composition as the result of in situ precipitation of certain solid materials during the blending of the oil and organic liquid/water phases. The solid precipitates employed must be insoluble in both the oil phase and the organic liquid/water phase, have a microscopically small particle size (average) on the order of 0.001 to 0.1 microns, and have a negative spreading coefficient so that they will be adsorbed on the interface of the oil and organic liquid/water phases. Various organic and inorganic salt precipitates are believed to meet these requirements and be suitable for use in carrying out the invention including the precipitation reaction products of soluble alginate, phosphate or sulfate with calcium chloride, e.g., calcium alginate, calcium phosphate, or calcium sulfate; of zinc salts with sodium stearate, e.g., zinc stearate; of sodium carboxymethylcellulose with zinc chloride, e.g., zinc carboxymethylcellulose; with each precipitate being used either alone or in combination with others.

Mostly preferred however, are the salt precipitates resulting from the reaction of calcium chloride and sodium silicate on the one hand e.g., calcium silicate; and calcium chloride and sodium dodecylbenzenesulfonate on the other hand e.g., calcium dodecylbenzenesulfonate, which have been found to be particularly satisfactory, especially when employed in combination. In practice, and as will be more fully described below, the calcium chloride, sodium silicate and sodium dodecylbenzenesulfonate reagents are added in solution form to the oil phase and organic liquid/water phase during blending thereof with the total amount of starting salt solution(s) being infuenced by several factors. One such factor relates to the observation that the precipitated insoluble calcium silicate particles enhance the temperature stability of the dispersed oil spheres whereas the precipitated calcium dodecylbenzenesulfonate particles enhances dimensionable stability thereof. Thus, when used in combination, the relative amounts of reagent solution forming each of these precipitates, respectively, may be adjusted via trial and error to achieve a desired balance between these effects leading to long term stability of the dispersed oil droplets. Also, it has been found that when different fragrance compounds are added to the organic liquid/water phase, additional adjustment of the quantity ratio between the mostly preferred salt precipitates, as well as of the total aggregate amount of these same salt precipitates, will be required to preserve a given oil droplet size, i.e., droplet size not only is dependent upon the total amount of insoluble material adsorbed at the interface between the oil phase and organic liquid/water phase, but furthermore, is sensitive to and influenced by the particular fragrance compound(s) added to the organic liquid/water phase. These considerations are further illustrated by the examples set forth in Table I below which show the amounts (percent by weight) of each of the mostly preferred starting salt solutions (precipitation reagents) required to formulate three different "cologne splash" compositions in accordance with the invention, wherein each formula has a different fragrance compound identified as "A", "B", and "C" respectively, and wherein each formula results in a composition having dispersed oil droplets whose average size varies in the range from about 1 to about 5 mm in diameter.

TABLE I

| Ingredient | Formula "A" | Formula "B" | Formula "C" |
|---|---|---|---|
| Light Mineral Oil | 35.0000% | 35.0000% | 35.0000% |
| Ethanol | 50.1000% | 51.1000% | 50.8600% |
| Water | 6.0340% | 0.3038% | 4.2942% |
| Fragrance | 5.0000% | 5.0000% | 5.0000% |
| Calcium Chloride (1%) | 1.0000% | 3.8500% | 2.0000% |
| Sodium Silicate (1%) | 1.5000% | 2.8350% | 2.0000% |
| Sodium Dodecylbenzene-sulfonate (10%) | 0.7500% | 0.9160% | 0.3750% |
| Colorants, U.V. Stablizer | Q.S. | Q.S. | Q.S |

TABLE I-continued

| Ingredient | Formula "A" | Formula "B" | Formula "C" |
| --- | --- | --- | --- |
| | 100.0000% | 100.0000% | 100.0000% |

The amount of starting salt solutions added to the composition will depend upon the amount of oil and fragrance, and the size of dispersed oil droplets, and may range up to 25% by weight with an amount in the range from about 1% to about 10% being mostly preferred.

Preferred two-phase compositions according to the present invention may be made by blending together the ingredients of Formulas "A", "B" and "C" of Table I. When this is done, the three salt solutions react with one another in situ to produce two precipitated insoluble salts namely, calcium silicate and calcium dodecylbenzenesulfonate which adhere to or are adsorbed at the interface of the oil and organic liquid/water phases, and one soluble salt, namely sodium chloride which passes harmlessly into solution. While it is true that the size of the resulting dispersed oil droplets may be controlled by adding more or less solid insoluble precipitate to the composition, other factors such as the rate of precipitation and severity of mixing during the processing stage can also affect droplet size. In addition, droplet size may be affected by the sequence in which the reagent starting salt solutions are mixed together during processing. These diverse factors will be more fully understood by reference to the following specific Examples which are illustrative and not limiting.

EXAMPLE 1

Formula "A" from Table I was used to form a composition according to the invention as follows. 5 parts of fragrance "A" were added to 50.1 parts of denatured alcohol (ethanol) and chilled and filtered in a side vessel. The contents were then fed to a main mixing vessel (100 gallon explosion-proof Tote) in which 1 part 1% calcium chloride salt solution and 0.056 parts U.V. stabilizer and colorants were added. In another side vessel, 35 parts of light mineral oil and 0.56 parts colorants were mixed and the contents added to the main mixing vessel. Continued mixing of the contents in the main mixing vessel under medium speed followed for a period of one (1) hour. In yet another side vessel, a pre-mix salt solution was prepared by adding together 6.035 parts demineralized water, 1.5 parts 1% sodium silicate salt solution, and 0.75 parts 10% sodium dodecylbenzenesulfonate solution, and mixing until uniform. The pre-mix salt solution batch was titrated into the main mixing vessel (Tote) through a metering pump over a 10 minute interval during which the tote mixing speed was set to 280 rpm. Mixing was continued for a period of one (1) hour following delivery of the pre-mix salt solution. The resulting batch was used to fill 1 oz. glass bottles which after remaining stationary for a period of 20 minutes respectively exhibited extremely clear, transparent oil spheres occupying the bottom-half of a clear colored liquid. The oil spheres were uniformly sized and measured about 3 mm in diameter. Vigorous shaking of the bottle caused the oil spheres to break up and cloud the liquid phase. After the bottle remained stationary for a period of 15-20 minutes, the oil spheres returned to their original size and disposition, indicating excellent reproducibility. Little or no sediment was observed within the bottle.

EXAMPLE 2

Formula "B" from Table I was used to form a composition according to the invention as follows. 5 parts of fragrance "B" were added to 51.1 parts of denatured alcohol (ethanol) and chilled and filtered in a side vessel. The contents were then fed to a main mixing vessel (100 explosion-proof Tote) in which 2.31 parts of 1% calcium chloride salt solution and 0.1592 parts U.V. stabilizer and colorants were added. In another side vessel, 35 parts of light mineral oil and 0.836 parts colorants were mixed and the contents added to the main mixing vessel. Continued mixing of the contents in the main mixing vessel under medium speed followed for a period of one (1) hour. In yet another side vessel, a first pre-mix salt solution was prepared by adding together 0.1430 parts demineralized water, 1.7010 parts 1% sodium silicate salt solution, and 0.5496 parts 10% sodium dodecylbenzenesulfonate salt solution, and mixing until uniform. The first pre-mix salt solution batch was titrated into the main mixing vessel through a metering pump over a 5 minute interval during which the Tote mixing speed was set to 190 rpm. Mixing was continued for a period of 15 minutes following delivery of the first pre-mix salt solution after which the batch in the main mixing vessel was allowed to settle for a further period of ½ hour. Mixing was then resumed for a 15 minute period at 190 rpm after which a second pre-mix salt solution batch comprising a uniform mixture of 0.08 parts demineralized water and 1.54 parts 1% calcium chloride salt solution was slowly added to the main mixing vessel over a 3–5 minute period followed by continued mixing for an additional 15 minute period. A third pre-mix salt solution batch comprising a uniform mixture of 0.08 parts demineralized water, 1.134 parts 1% sodium silicate salt solution, and 0.3664 parts 10% sodium dodecylbenzenesulfonate salt solution was slowly added to the main mixing vessel over a further 3–5 minute period followed by continued mixing for yet an additional one (1) hour period. The resulting batch was employed to fill 1 oz. glass bottles, the contents of which exhibited the same characteristics as the final composition of Example 1, except that the average size of the dispersed oil droplets was in the range of about 1 to about 2 mm in diameter.

EXAMPLE 3

Formula "C" from Table I was used to form a composition according to the invention as follows. 5 parts of fragrance "C" were added to 50.86 parts of denatured alcohol (ethanol) and chilled and filtered in a side vessel. The contents were then fed to a main mixing vessel (100 gallon explosion-proof Tote) in which 1.6 parts 1% calcium chloride salt solution and 0.138 parts U.V. stabilizer and colorants were added. In another side vessel, 35 parts of light mineral oil and 0.34 parts colorants were mixed and the contents added to the main mixing vessel. Continued mixing of the contents in the main mixing vessel under medium speed followed for a period of one (1) hour. In yet another side vessel, a first pre-mix salt solution was prepared by adding together 2.4942 parts demineralized water, 1.6000 parts 1% sodium silicate salt solution, 0.3000 parts 10% sodium dodecylbenzenesulfonate salt solution, and mixing until uniform. The first pre-mix salt solution batch was titrated into the main mixing vessel (Tote) through a metering pump over a 5 minute interval during which the Tote mixing speed was set to 190 rpm. Mixing was continued for a period of 15 minutes following delivery of the first pre-mix salt solution after which the batch in the main mixing vessel was allowed to settle for a further period of ½ hour. Mixing was then resumed for a 15 minute period at 190 rpm after which a second pre-mix salt solution batch comprising a uniform mixture of 0.9 parts demineralized water and 0.4 parts 1% calcium chloride salt solution were slowly added to the main mixing vessel over a 3-5 minute period followed by continued mixing for an additional 15 minute period. A third pre-mix salt solution batch comprising a uniform mixture of 0.9 parts demineralized water, 0.4 parts 1% sodium silicate salt solution, and 0.075 parts 10% sodium dodecylbenzenesulfonate salt solution were slowly added to the main mixing vessel over a further 3-5 minute period followed by continued mixing for yet an additional one (1) hour period. The resulting batch was used to fill 1 oz. bottles, the contents of which exhibited the same characteristics as the final compositions of Examples 1 and 2 except that the average oil droplet size was in the range of about 2 to about 3 mm in diameter.

From the foregoing, it is evident that the present invention provides a novel two-phase cosmetic preparation and method of preparing same. As a result of employing the technique of in situ precipitation of insoluble solid particles adsorbed at the interface between the oil phase and organic liquid/water phase, there is provided an aesthetically appealing cosmetic composition whose dispersed oil droplets are extremely clear and transparent to the naked eye, have excellent longevity and reproducibility over an extended period of time, and which exhibits little or no sedimentation of solid particles. And although various specific Examples have been described to illustrate the best mode of carrying out the invention, it will be appreciated that many modifications may be made. For example, instead of using a fragrance compound dissolved in the organic liquid/water phase other cosmetic ingredients miscible with either the oil phase or the organic liquid phase may be used instead such as skin lotions, hair preparations, and the like. Still further, it is possible to add interesting visual effects to the composition by using different colorants added to each phase respectively, i.e., the oil spheres may be one color whereas the organic liquid may be another contrasting or harmonizing color. Obviously, other alterations will be evident to those skilled in the art and accordingly, the present invention should be limited only by the true spirit and scope of the appended claims.

We claim:

1. A liquid cosmetic composition comprising:
   up to about 95% by weight of an organic liquid phase comprised of at least one member selected from the group consisting of monohydric alcohols having carbon atoms of no greater than 5, polyhydric alcohols having carbon atoms of no greater than 6, polyethylene glycol having carbon atoms of no greater than 50, ethers having carbon atoms of no greater than 6, and ketones having carbon atoms of no greater than 6;
   up to about 80% by weight of an oil phase in the form of stable spheres or droplets dispersed in said organic liquid phase, said oil phase being comprised of at least one member selected from the group consisting of mineral oil, liquid paraffin, squalane, 2-hexyldecyl palmitate, 2-octylododecyl myristate, di-2-hexyldecyl adipate, di-2-ethylhexyl sebacate, olive oil, tsubaki oil, mink oil, isostearic acid, oleic acid, oleyl alcohol and a polypropyleneglycol butyl ether having a polymerization degree of approximately 40; and
   not greater than approximately 25% by weight of finely divided solid particles insoluble in said organic liquid phase and said oil phase, said solid particles comprising one or more precipitated salts selected from the group consisting of the reaction products of soluble alginate, phosphate or sulfate with calcium chloride;, of zinc salts with sodium stearate; of carboxymethylcellulose with zinc chloride; of calcium chloride with sodium silicate; and of calcium chloride with sodium dodecylbenzenesulfonate.

2. The composition of claim 1 wherein said precipitated salt is calcium silicate.

3. The composition of claim 1 wherein said precipitated salt is calcium dodecylbenzenesulfonate.

4. The composition of claim 1 wherein said precipitated salt is selected from the group consisting of calcium silicate and calcium dodecylbenzenesulfonate.

5. The composition of claim 1 wherein said precipitated salt has an average particle size substantially less than 1 micron.

6. The composition of claim 1 wherein said organic liquid phase comprise ethanol and at least one cosmetic ingredient.

7. The composition of claim 6 wherein said cosmetic ingredient is a fragrance compound.

8. The method of making a liquid cosmetic composition of the two-phase type comprising the steps of:
   (a) mixing together an oil phase and an immiscible organic liquid phase, said oil phase comprising one or more members selected from the group consisting of mineral oil, liquid paraffin, squalane, 2-hexyldecyl palmitate, 2-octyldodecyl myristate, di-2-hexyldecyl adipate, di-2-ethylhexyl sebacate, olive oil, tsubaki oil, mink oil, isostearic acid, oleic acid, oleyl alcohol and a polypropyleneglycol butyl ether having a polymerization degree of approximately 40; said organic liquid phase comprising at least one member selected from the group consisting of monohydric alchols having carbon atoms of no greater than 5, polyhydric alcohols having carbon atoms of no greater than 6, polyethylene glycol having carbon atoms of no greater than 50, ethers having carbon atoms of no greater than 6, and ketones having carbon atoms of no greater than 6;
   (b) adding a first salt precipitation reaction product to the mixture of step (a), said first salt precipitation reaction product comprising at least one member selected from the group consisting of soluble alginate, phosphate or sulfate; zinc salts; carboxymethylcellulose; and calcium chloride;
   (c) adding a second salt precipitation reaction product to the mixture of step (a), said second salt precipitation reaction product comprising at least one member selected from the group consisting of calcium chloride, sodium stearate, zinc chloride, sodium silicate and sodium dodecylbenzenesulfonate, wherein said first and second salt precipitation reaction products react to form a solid precipitate salt insoluble in either said oil phase or said organic liquid phase, said solid precipitate salt being absorbed at the interface of said oil and organic liquid phases, to form stable spheres or droplets of said oil phase dispersed in said organic liquid phase.

9. The method of claim 8 further comprising the step of adding a third salt precipitation reaction product comprising at least one member selected from either of the groups set fourth in step (c) above to the mixture of step (a) wherein at least two different solid precipitate salts are adsorbed at the interface of said oil and organic liquid phases.

* * * * *